(12) United States Patent
Raykhfeld et al.

(10) Patent No.: US 10,843,216 B2
(45) Date of Patent: Nov. 24, 2020

(54) FLUID DISPERSION NOZZLE

(71) Applicant: ECO SHIELD ENGINEERING LLC, Eagan, MN (US)

(72) Inventors: Yevgeniy Raykhfeld, Eagan, MN (US); Igor Golenistsev, Eagan, MN (US)

(73) Assignee: Eco Shield Engineering LLC, Eagan, MN (US)

( * ) Notice: Subject to any disclaimer, the term of this patent is extended or adjusted under 35 U.S.C. 154(b) by 0 days.

(21) Appl. No.: 16/096,689

(22) PCT Filed: Apr. 26, 2017

(86) PCT No.: PCT/US2017/029691
§ 371 (c)(1),
(2) Date: Oct. 25, 2018

(87) PCT Pub. No.: WO2017/189759
PCT Pub. Date: Nov. 2, 2017

(65) Prior Publication Data
US 2019/0321846 A1 Oct. 24, 2019

Related U.S. Application Data

(60) Provisional application No. 62/327,987, filed on Apr. 26, 2016, provisional application No. 62/327,679, filed on Apr. 26, 2016.

(51) Int. Cl.
*B05B 13/00* (2006.01)
*B05B 7/00* (2006.01)
(Continued)

(52) U.S. Cl.
CPC ......... *B05B 13/005* (2013.01); *A01M 7/0032* (2013.01); *B05B 7/0075* (2013.01); *B05B 17/06* (2013.01); *A61L 9/14* (2013.01)

(58) Field of Classification Search
CPC ..... B05B 7/0075; B05B 13/005; B05B 17/06; B05B 17/0692; A01M 7/0014;
(Continued)

(56) References Cited

U.S. PATENT DOCUMENTS 3,341,081 A 9/1967 King
3,698,644 A 10/1972 Nystuen
(Continued)

FOREIGN PATENT DOCUMENTS

| EP | 2581137 A1 | 4/2013 |
|---|---|---|
| GB | 1156259 A | 6/1969 |
| RU | 2262393 C1 | 10/2005 |

OTHER PUBLICATIONS

International Search Report for PCT/US2017/029681, dated Sep. 28, 2017, 4 pages.
(Continued)

*Primary Examiner* — Darren W Gorman
(74) *Attorney, Agent, or Firm* — Cozen O'Connor

(57) ABSTRACT

A fluid dispersion nozzle and system for spraying large areas with near-monodispersed, aerosolized fluid droplets. More specifically, the fluid dispersion nozzle receives pressurized and fluid from fluid dispersion machinery, aerosolizes the fluid into near-monodispersed droplets, and distributes the aerosolized, near-monodispersed droplets evenly over long distances. The nozzle is an adjustable, dual-contour, supersonic nozzle that includes a main adjustable contour, an auxiliary contour, an axial fluid injector, a resonator, and a plunger.

12 Claims, 8 Drawing Sheets

(51) Int. Cl.
*A01M 7/00* (2006.01)
*A61L 9/14* (2006.01)
*B05B 17/06* (2006.01)

(58) Field of Classification Search
CPC ..... A01M 7/0032; A01M 7/0042; A61L 2/18; A61L 9/14
See application file for complete search history.

(56) References Cited

U.S. PATENT DOCUMENTS

| | | | |
|---|---|---|---|
| 3,735,778 A * | 5/1973 | Garnier | B05B 7/0075 137/896 |
| 4,317,308 A | 3/1982 | Derrick et al. | |
| 4,932,591 A * | 6/1990 | Cruz | B05B 1/265 239/498 |
| 4,992,206 A | 2/1991 | Waldron | |
| 5,248,448 A | 9/1993 | Waldron et al. | |
| 5,296,702 A | 3/1994 | Beck et al. | |
| 5,522,930 A | 6/1996 | Modera et al. | |
| 5,713,521 A | 2/1998 | Scheffel | |
| 5,860,598 A * | 1/1999 | Cruz | B05B 7/0075 239/346 |
| 6,152,382 A * | 11/2000 | Pun | A01M 7/0014 239/11 |
| 6,203,186 B1 | 3/2001 | Cruz | |
| 8,655,559 B2 | 2/2014 | Peake et al. | |
| 2002/0030117 A1 | 3/2002 | Bryan et al. | |
| 2002/0100815 A1 | 8/2002 | Doebler et al. | |
| 2006/0131348 A1 | 6/2006 | Gould et al. | |
| 2009/0025794 A1 | 1/2009 | Dorendorf et al. | |
| 2016/0136672 A1 | 5/2016 | Doswell et al. | |
| 2018/0111148 A1 | 4/2018 | Batcheller et al. | |

OTHER PUBLICATIONS

International Search Report for PCT/US2017/029691, dated Jul. 27, 2017, 2 pages.
Written Opinion for PCT/US2017/029681, dated Sep. 28, 2017, 5 pages.
Written Opinion for PCT/US2017/029691, dated Jul. 27, 2017, 4 pages.
U.S. Appl. No. 16/096,688.
Non-Final Office Action in U.S. Appl. No. 16/096,688, dated Sep. 16, 2020, 16 pages.

\* cited by examiner

FLUID DISPERSION NOZZLE

CROSS-REFERENCE TO RELATED APPLICATION

This application claims the benefit of U.S. Provisional Application No. 62/327,987, filed Apr. 26, 2016 and titled FLUID DISPERSION NOZZLE, and claims the benefit of U.S. Provisional Application No. 62/327,679, filed Apr. 26, 2016 and titled METHOD AND SYSTEM FOR FLUID DISPERSION, which, along with the subject matter disclosed in PCT Application No. PCT/US17/29681, filed Apr. 26, 2017 and titled PRODUCT DELIVERY METHOD TO THE TREATMENT OBJECT AND THE DEVICE FOR ITS IMPLEMENTATION are hereby incorporated by reference, with such incorporation limited such that no subject matter is incorporated that is contrary to the explicit disclosure herein.

FIELD OF THE DISCLOSURE

The disclosed invention relates to a fluid dispersion nozzle for spraying and dispersing fluid over large areas of land. More specifically, the disclosed invention relates to a fluid dispersion nozzle that creates and distributes a cloud of aerosolized, polydispersed and/or near-monodispersed droplets by receiving pressurized fluid and air from a fluid pump and air compressor, using the pressurized air to redirect and collide the pressurized fluid particles with solid surfaces in the nozzle, and dispersing aerosolized droplets over an agricultural field.

BACKGROUND OF THE INVENTION

There are several situations in which a fluid needs to be sprayed over large areas of land. For example, spraying is currently used for protection in agricultural and forestry activities, to control wild plants for zero tillage farming, to control psychoactive plants, to manage pests in insecticidal processing, to apply fertilizer to plants' leaves, to deliver fertilizer through stalks and leaves, to desiccate plants, to treat plants with fungicides, and to sanitize indoor structures in the case of animal husbandry.

However, current dispersers are limited in the range in which they can reach and the method of fluid application to the plants or other objects. Additionally, they unevenly cover the surfaces or structures being sprayed, waste the fluid being dispersed, and create environmental hazards through, for example, runoff or waste of excess chemicals. Therefore, a fluid dispersion system and method is needed that is capable of spraying and dispersing fluid materials evenly, over longer distances, and without unnecessary chemical waste.

SUMMARY OF THE INVENTION

The present disclosure is a fluid dispersion nozzle and system for spraying large areas of agricultural fields, forests, and indoor structures with polydispersed and/or near-monodispersed, aerosolized fluid droplets. More specifically, the fluid dispersion nozzle receives pressurized air and fluid from fluid dispersion machinery, aerosolizes the fluid into polydispersed and/or near-monodispersed droplets, and distributes the aerosolized, polydispersed and/or near-monodispersed droplets evenly over long distances. The nozzle is an adjustable, dual-contour, supersonic nozzle that includes a main adjustable contour, an auxiliary contour, and an axial fluid injector.

DETAILED DESCRIPTION

Figure 1:
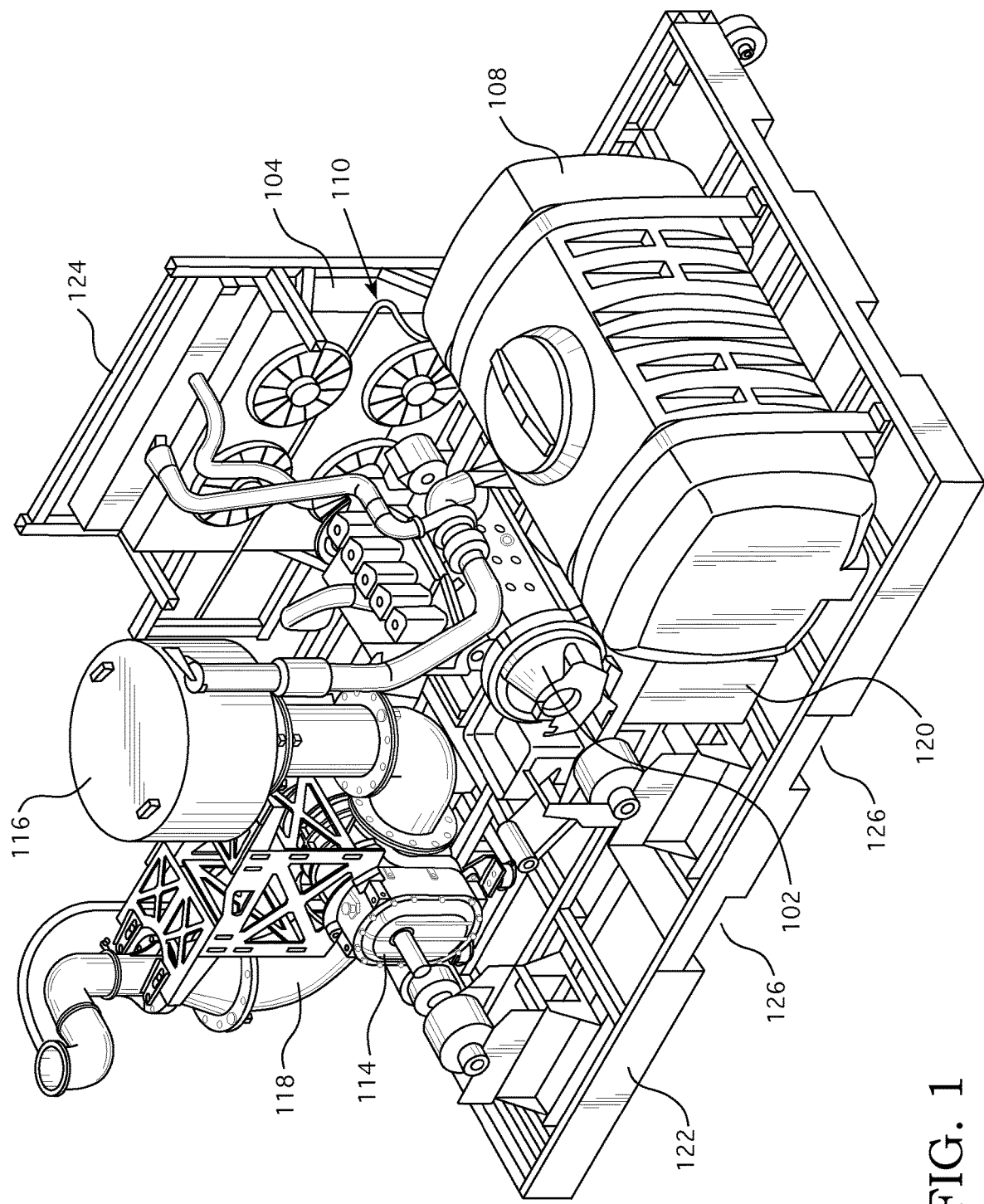
FIG. 1 is a perspective view of fluid dispersion machinery according to one embodiment of the disclosed invention.

The present disclosure relates to a fluid dispersion nozzle and system used to create and distribute a cloud of polydispersed and/or near-monodispersed droplets of fluid. Various embodiments of the fluid dispersion nozzle and related system will be described in detail with reference to the drawings, wherein like reference numerals represent like parts and assemblies throughout the several views. Reference to various embodiments does not limit the scope of the fluid dispersion nozzle and related system disclosed herein. Additionally, any examples set forth in this specification are not intended to be limiting and merely set forth some of the many possible embodiments for the fluid dispersion nozzle and related system. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

The disclosed fluid dispersion system is comprised of a fluid dispersion machine that accelerates fluid and air particles and a fluid dispersion nozzle that aerosolizes the fluid particles by combining them with the accelerated air particles. More specifically, the fluid dispersion machinery and nozzle function together to combine fluid materials with pressurized air, which results in the aerosolization of the fluid and enables the aerosolized fluid particles to travel long distances. For example, in a preferred embodiment, the fluid may exit the nozzle in five to 150 micron droplets and may be capable of traveling up to two miles.

The design of the fluid dispersion nozzle and machinery enables dispersion of a near-monodispersed aerosol; use of wide-range nozzles; and a high aerosol flow range based on the parameters of the air fed to the nozzle. The results are obtained by eliminating cluttering of the air and fluid flow in the nozzle. More specifically, clutter of air and fluid is eliminated in the nozzle by maintaining consistent fluid pressure in the nozzle.

The practical use of the invention will allow for efficient and quality fluid dispersion by creating an aerosol of the required droplets size that can travel extended distances and be affected by temperature inversions.

Method

The fluid is sprayed by creating a cloud of polydispersed or near-monodispersed droplets of physiologically active agents in the atmosphere (for example, the troposphere). The fluid that is sprayed can be fertilizer, fungicides, herbicides, insecticides, disinfectants, or other chemical, biological, and mineral-based significant fluids. The same components and processes can be used to disperse any fluid regardless of the density and viscosity of the fluid. Due to the fine particle size created by the disclosed nozzle and system, the fluid can travel extremely far distances. In some embodiments, after the fluid exits the fluid dispersion system, it is in the form of polydispersed or near-monodispersed droplets (for example, droplets with diameters between five and 150 microns). In other embodiments, the fluid exits the fluid dispersion system in the form of monodispersed droplets. This dispersion method results in less fluid being used compared to pre-existing fluid dispersion systems, which lessens the impact of active chemicals on the environment and decreases costs associated with situations and settings where fluid dispersion is typically used. For example, fluid dispersion is frequently used for maintenance of plants and animals in an agricultural setting, for forest protection, for treatment of indoor structures, and for vector disease control. All of these scenarios could benefit from the disclosed fluid dispersion nozzle and system.

While the current disclosure primarily describes use of the method, fluid dispersion nozzle and fluid dispersion machinery in a plant-growing context, the same machines and methods may be implemented in livestock equipment and premises, forest protection, indoor treatment of structures, and vector disease control. In this context, the chemicals used may be disinfectants and the use of disinfectants with the disclosed machine and methods may also result in the benefit of reduced amounts of chemicals used and better application to desired surfaces.

Figure 9:
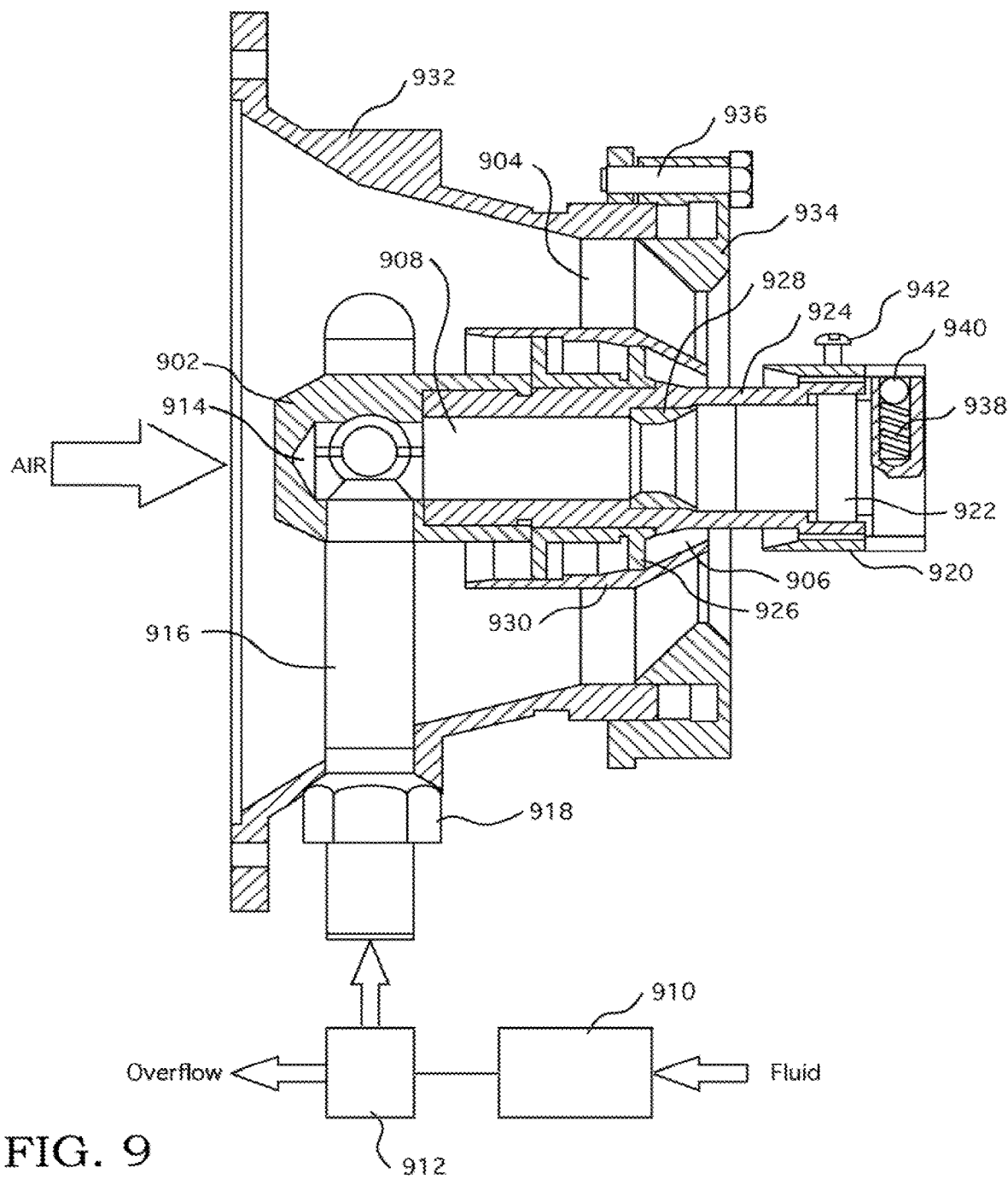
FIG. 9 is a side cross-sectional view of a fluid dispersion nozzle according to one embodiment of the disclosed invention.
Figure 10:
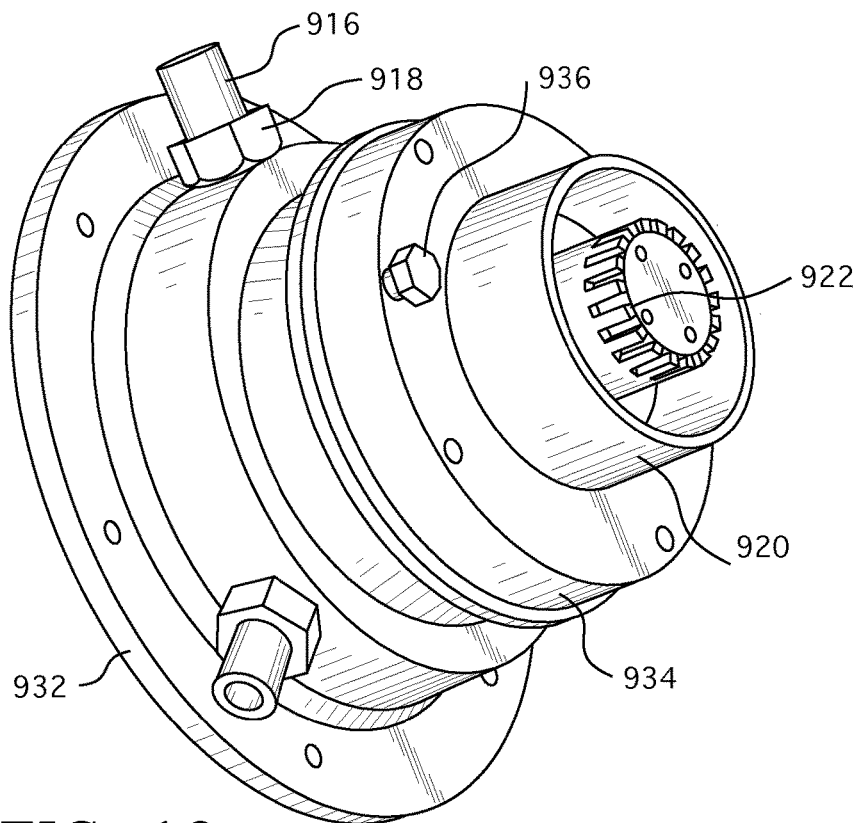
FIG. 10 is a front perspective view of the fluid dispersion nozzle of FIG. 9.
Figure 11:
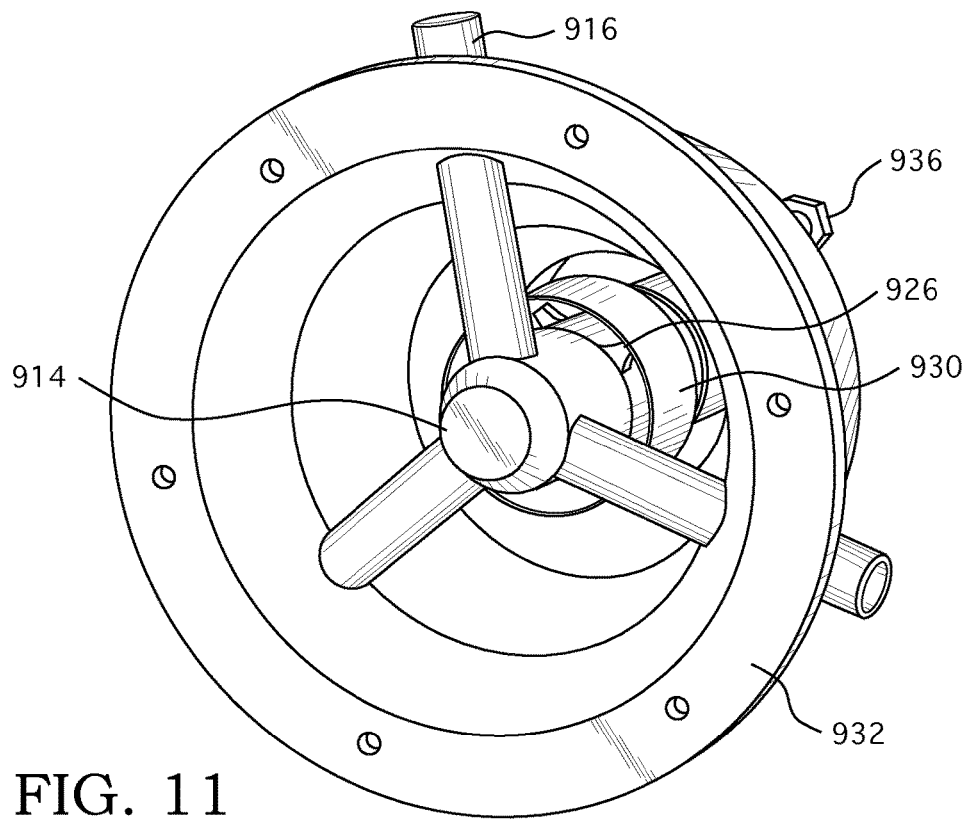
FIG. 11 is a rear perspective view of the nozzle of FIG. 9.
Figure 12:
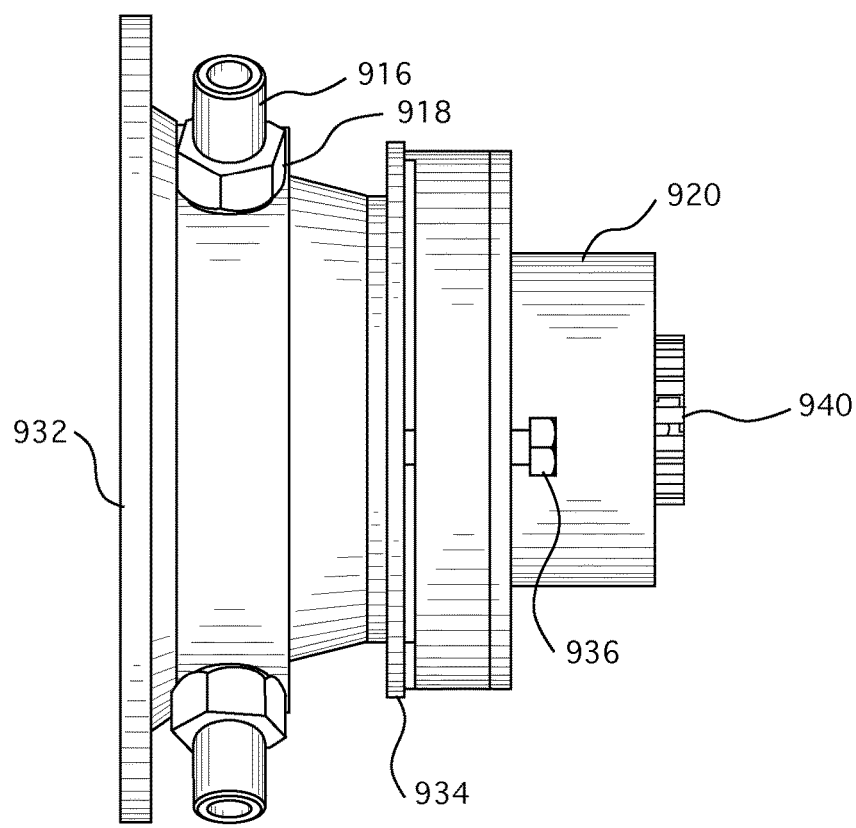
FIG. 12 is a side view of the nozzle of FIG. 9.
Figure 13:
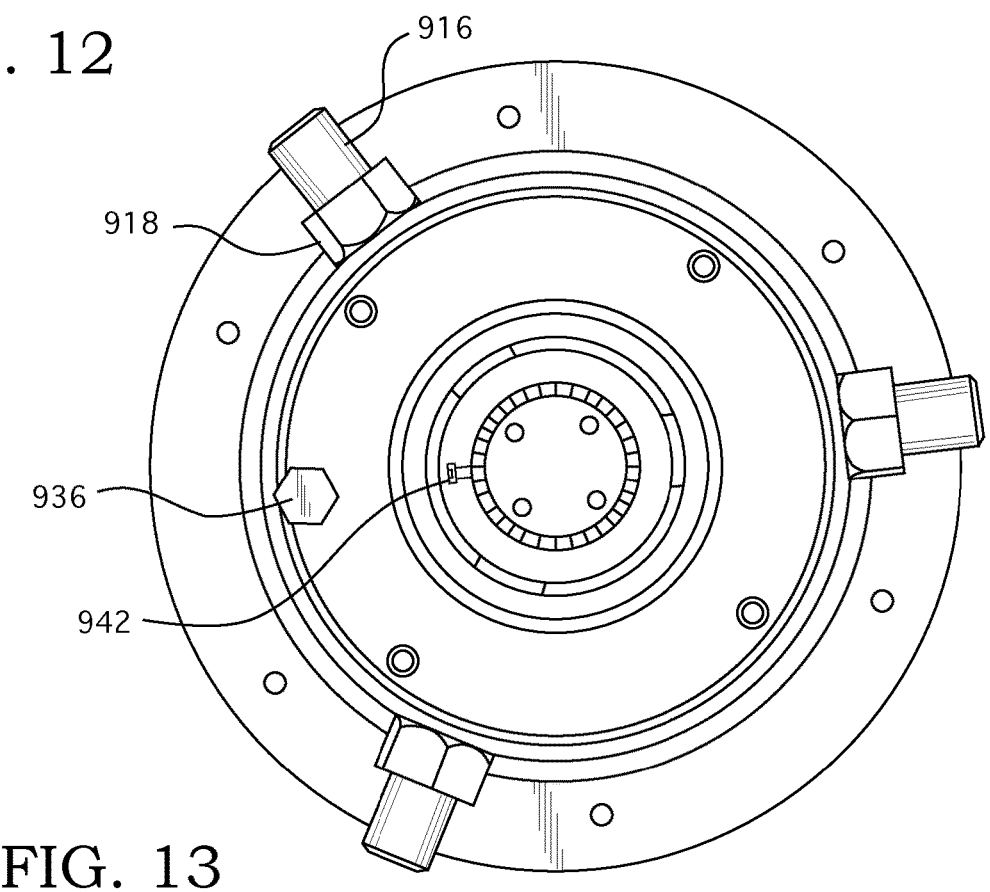
FIG. 13 is a front view of the nozzle of FIG. 9.

Generally, the method of fluid dispersion is comprised of fluid flow from a fluid pump 112, airflow from an air compressor 114, acceleration of airflow in the nozzle, and combination of the fluid and accelerated airflow in the nozzle resulting in an aerosol. The aerosol's dispersion can be adjusted by changing the discharge rates of the fluid or the air. For example, the fluid discharge rate can be smoothly changed from an axial fluid injector 908, illustrated in FIG. 9, and the air discharge rate can be smoothly adjusted by discretely changing the airflow rate from a main adjustable contour 904 and a auxiliary contour 906, also illustrated in FIG. 9.

While the discharge rates of the fluid and air may be adjusted, in a preferred embodiment, the pressure of the fluid flow in the axial fluid injector 908 is maintained at a constant rate. Further, the maximum flow rate can be maintained within a specified range regardless of the preset range of the flow amount. For example, when the fluid flow rate increases from the fluid dispersion machinery to the fluid dispersion nozzle, the fluid flow pressure is maintained by increasing the fluid flow rate out of the nozzle. More specifically, the decrease in the specific energy of the aerosol dispersion in the field of ultrasound air fluctuations in the supersonic jet from the nozzle's auxiliary contour 906 due to an increase in fluid flow rate to the nozzle is compensated by an increase in fluid flow rate out of the nozzle.

The method of fluid dispersion out of the nozzle is comprised of: (1) injecting fluid at a high velocity through the center of the nozzle; (2) allowing the fluid to hit various barriers at the end of the nozzle that break the fluid particles into smaller fluid particles; (3) enabling the smaller fluid particles to escape through a side of the center portion of the nozzle; (4) combining the escaped fluid with air flowing through an auxiliary contour 906, wherein the air from the auxiliary contour 906 pushes the smaller fluid particles in a direction parallel with their original orientation; (5) allowing the smaller fluid particles to hit a second barrier near the end of the nozzle that breaks the smaller fluid particles into near-monodispersed droplets; (6) enabling the near-monodispersed droplets to reflect laterally away from the center of the nozzle; (7) combining the near-monodispersed droplets with air flowing through a main adjustable contour 904 of the nozzle, wherein the air pushes the near-monodispersed droplets forward away from the nozzle and permits the near-monodispersed droplets to travel as a cloud for an extended distance (for example, hundreds or thousands of yards).

While typical fluid dispersion methods for agricultural fields involve spraying the fluid during the day and pushing the fluid down onto the plant using gravitational forces, the disclosed method involves spraying the fluid during the night and allowing gravitational forces and natural temperature inversions to pull the cloud down onto the plant. More specifically, because of the minute size of the fluid particles, the fluid droplets can effectively travel for miles. Therefore, to control for placement of the fluid droplets over agricultural fields, the dispersion process ideally takes place at night when (1) overnight radiative cooling of surface air results in a nocturnal temperature inversion where the air temperature near the ground is cooler than the air temperature near the top of a plant and (2) there is a very small, constant wind speed that can carry the fluid droplets for a limited amount of time before they are pulled onto the plants. Accordingly, when the near-monodispersed cloud of fluid droplets is ejected by the disclosed nozzle and is hovering in the air near the tops of plants, the natural air inversion process will pull the fluid down and cover the remainder of the plants.

Fluid Dispersion Nozzle

As briefly mentioned above, fluid travels through the nozzle and is broken into smaller fluid droplets by physical impact with surfaces on the nozzle. In some embodiments, the nozzle is connected to fluid dispersion machinery, wherein the fluid dispersion machinery includes an engine 102, a fluid pump 112 that supplies fluid to the nozzle, an air compressor 114 that supplies pressurized air to the nozzle, and other components that help provide high velocity air and fluid to the nozzle. The combination of the method and the nozzle enable quality and highly efficient fluid dispersion with the highest possible degree of droplets' monodispersity.

Generally, the nozzle is a supersonic, adjustable, dual-contour nozzle connected to an air compressor 114 and a fluid pump 112, and is comprised of several components. In a preferred embodiment, the nozzle, illustrated in FIGS. 9-13, can be comprised generally of a nozzle body 902 connected to the fluid dispersion machinery, two contours for airflow such as a main adjustable contour 904 and an auxiliary contour 906, an axial fluid injector 908 for fluid flow, and a resonator 920 for aerosolizing the fluid. The axial fluid injector 908 may be primarily contained within a hollow tip of the nozzle body 914, which can be centered in the nozzle and further connected to the fluid injector body 924 and to the nose cone 930 via the spacer 926, which can be centered accurately along the axis of the axial fluid injector 908.

In some embodiments, fluid may be initially pumped from a fluid tank 108 through a fluid pump 910, through a pressure-regulating valve 912, through a hollow pylon 916 attached to the nozzle via a nut 918, and into the hollow tip of the nozzle body 914 that may be one component of the axial fluid injector 908. In some embodiments, the axial fluid injector 908 can adjust the fluid flow. In some embodiments, there is one pylon 916 through which fluid enters the axial fluid injector 908. In other embodiments, there may be a plurality of pylons 916 (for example, three) through which fluid enters the axial fluid injector 908. The pressure-regulating valve 912 can maintain the fluid pressure consistency of a predetermined rate. This rate may maximize the level of hydraulic energy, which can maximize the speed of the fluid from the axial fluid injector 908.

In a preferred embodiment, once the fluid flows into the hollow tip of the nozzle body 914 that is part of the axial fluid injector 908, it can progress through the hollow tip of the nozzle body 914 at high velocity and come into contact with a resonator 920 and plunger 922. The resonator 920 may be a high-speed resonator that redirects the fluid in order to decrease the size of the fluid particles. In some embodiments, the resonator 920 has 14 to 36 axial slots interfaced with a metal ball-lock located in the plunger 922. The resonator 920 can be attached to the fluid injector body 924 from the outside via a threaded connection, such as screw 942, and the plunger 922 can be attached to the fluid injector body 924 from the inside via a threaded connection.

The plunger 922 can be interfaced with a saddle 928 on the conical surface of the contact type (for example: cone—torus). The interface of the plunger 922 with the saddle 928 can ensure that the in-line, axial slot is opened accurately in the contact consistent with the conicity of the saddle 928. In some embodiments, a ball 940, such as a steel ball, can be pushed by a spring 938 toward the outer wall of the resonator 920 and can engage with each of the resonator's 14 to 36 axial slots. Therefore, the ball 940 can lock the plunger 922 in place in a specific position relative to the resonator 920 each time the plunger 922 is rotated and the ball 940 lands between in-line slots. In some embodiments, when the plunger 922 is turned by one slot relative to the resonator 920, the in-line slot can be opened at, for example, 0.0014÷0.0022 mm, and when the plunger 922 is turned by one revolution relative to the resonator 920, the in-line slot can be opened at, for example, 0.05÷0.08 mm. A preferred embodiment of the disclosed invention involves activation of the nozzle when the ball 940 is rotated through the first six axial slots.

When the fluid flows through the axial fluid injector 908, it comes into contact with the plunger 922 and resonator 920 and is reduced in size. More specifically, the fluid can first hit the plunger 922, break into smaller, fluid particles, and reflect off the plunger 922 to then be redirected out of the axial fluid injector 908 through at least one hole in the side the fluid injector body 924 at, for example, a location behind the resonator 920. This hole, in some embodiments, may be variable in size and may be controlled by rotation of the plunger 922, as described above. After the fluid particles exit through the at least one hole in the side of fluid injector body 924, they can come into contact with air flowing through the auxiliary contour 906, be directed forward toward the resonator 920, hit the resonator 920 between its inner wall and the outer wall of the fluid injector body 924, be reduced in size even further, reflect off and out of the resonator 920, come into contact with air flowing through the main adjustable contour 904, and be dispersed forward past the end of the nozzle and into the atmosphere as a near-monodisperse cloud. In a preferred embodiment, the fluid droplets are fragmented by the mechanical impact of the semi-fixed surfaces, which are vibrating with a forced ultrasound frequency of the fluid injector body 924 and resonator 920 that is caused by the impact of the ultrasonic air fluctuation.

As briefly mentioned above, the nozzle is preferably a dual-contour nozzle that includes a main adjustable contour 904 and an auxiliary contour 906, both of which can surround the axial fluid injector 908, which may be centered in the nozzle. The auxiliary contour 906 is designed to aerosolize the fluid from the axial fluid injector 908 by, in some embodiments, combining the fluid with ultrasound waves generated by airflow from the auxiliary contour 906 to the resonator 920. The main adjustable contour 904 is designed for final fluid dispersion by, for example, using airflow through the main contour 904 to blow the fluid aerosol out to the atmosphere in the form of a cloud. The main adjustable contour 904 and the auxiliary contour 906 can have critical cross-sections that, in a preferred embodiment, are adjustable.

The main adjustable contour 904 can be, in some embodiments, defined as the space between the outer parts of the nozzle and the inner parts of the nozzle. More specifically, the outer parts of the nozzle that define the outer boundary of the main adjustable contour 904 can include the nozzle body 902, the disperser body 932, and the nozzle head 934, which may be held in place by a clamping screw 936. The inner parts of the nozzle that define the inner boundary of the main adjustable contour 904 can include the hollow tip of the nozzle body 914, the nose cone 930, and the fluid injector body 924.

The auxiliary contour 906 can be, in some embodiments, defined as the space between the axial fluid injector 908 and the nose cone 930, which may be close-fitted on front and rear stationary blades of a spacer 926. More specifically, the nose cone 930 can define the outer boundary of the auxiliary contour 906, and the hollow tip of the nozzle body 914 and the fluid injector body 924 can define the inner boundary of the auxiliary contour 906.

As previously described, to aerosolize the fluid and disperse it over an agricultural field, the nozzle can receive fluid and pressurized air and can enable hydraulic fluid fragmentation of the fluid to create droplets. More specifically, initial pneumatic dispersion of the fluid droplets can occur using ultrasound air fluctuations of the supersonic jet from the auxiliary contour 906, and the aerosol's final pneumatic dispersion can occur using a supersonic air jet from the main adjustable contour 904 of the nozzle, which supplies the aerosol to the site of application. The aerosol's dispersion may be adjusted by discretely changing the airflow from the auxiliary contour 906 and by the main adjustable contour 904.

In some embodiments, air can enter from the back of the adjustable, dual-contour nozzle and can be accelerated (for example, up to the speed of sound) through the main adjustable contour 904 and the auxiliary contour 906 due to a decrease in available volume and, therefore, a decrease in pressure. For example, the nozzle can be connected to an air compressor, which feeds the air to the nozzle under pressure, thereby enabling and ensuring a supercritical pressure differential in the nozzle.

As described above, it is the combination of air and fluid that create the aerosolized, near-monodispersed droplets capable of traveling long distances. Therefore, the nozzle is dedicated to decreasing the size of the fluid particles and projecting them out from the nozzle using pressurized and accelerated air.

Air can flow through the auxiliary contour 906 and combine with fluid that reflects off of the plunger 922 and exits the axial fluid injector 908. Due to the high velocity of air speed proceeding through the auxiliary contour 906, the fluid that exits the axial fluid injector 908 can be redirected at high velocity into the resonator 920 and reflected off of the resonator 920. Therefore, the fluid droplets are preferably dispersed into an aerosol by the pneumatic impact in the field of ultrasound air fluctuations of the supersonic jet from the auxiliary contour 906, which can be generated by the resonator 920 and activated by a motor.

At the same time air is flowing through the auxiliary contour 906, air can also be flowing at high velocity through the main adjustable contour 904. Due to the high velocity of air as it proceeds through the main adjustable contour 904, the fluid that reflects off of the resonator 920 can combine with the air proceeding through the main adjustable contour 904 and then be dispersed into the atmosphere. Therefore, for the final pneumatic dispersion, the aerosol can be directed into the supersonic airflow from the main adjustable contour 904, where it receives the required dispersion and near-monodispersion rates. The supersonic air from the nozzle can then distribute the aerosol to the place of its application.

Aerosol dispersion, including near-monodispersion, may be managed by smoothly changing the fluid flow and the airflow. The change in fluid flow can occur by rotating the plunger 922, and the change in airflow can occur by turning a nut on the main adjustable contour 904. The multiplier impact of the hydraulic and pneumatic fragmentation of the fluid, which is accomplished by combining the variables and individual impacts, can allow for adjusting the aerosol near-monodispersion level while keeping the dispersion rate unchanged.

Fluid Dispersion Machinery

Figure 8:
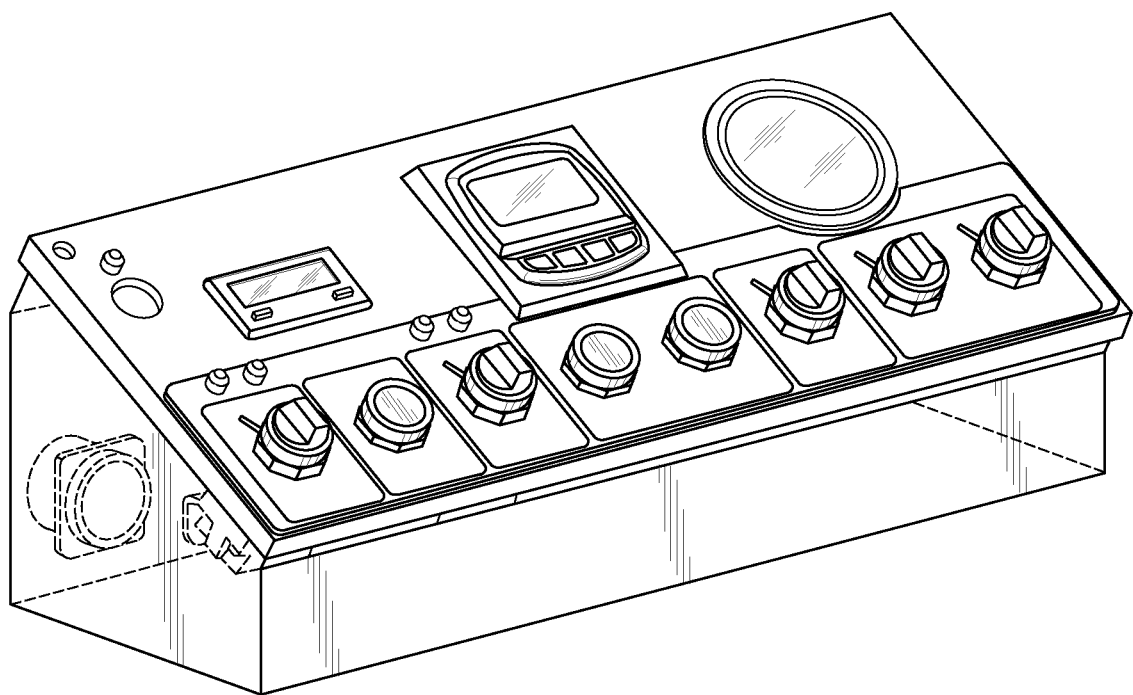
FIG. 8 illustrates a control system for a fluid dispersion nozzle and the fluid dispersion machinery according to one embodiment of the disclosed invention.

As described above, the fluid dispersion nozzle can receive fluid and air at high velocities from fluid dispersion machinery. Generally, the machinery in the support system is comprised of a combustion engine-driven fluid pump and air compressor that take fluid from a fluid reservoir and air from the atmosphere and pressurize the corresponding fluid and air before feeding them into the fluid dispersion nozzle. In some embodiments, the fluid dispersion machinery is capable of being transported and operated on a vehicle. For example, the machinery may be mounted in the open bed of a truck, enabling a user to drive the truck around or through an agricultural field, an open field, a forest, or an enclosed structure while employing the machinery and fluid dispersion nozzle. The machinery can interface with a remote control console, as illustrated in FIG. 8, that allows for control of engine speed and liquid injection flow as well as basic operational feedback. The remote control console can enable control from the cab of the transport truck.

Figure 2:
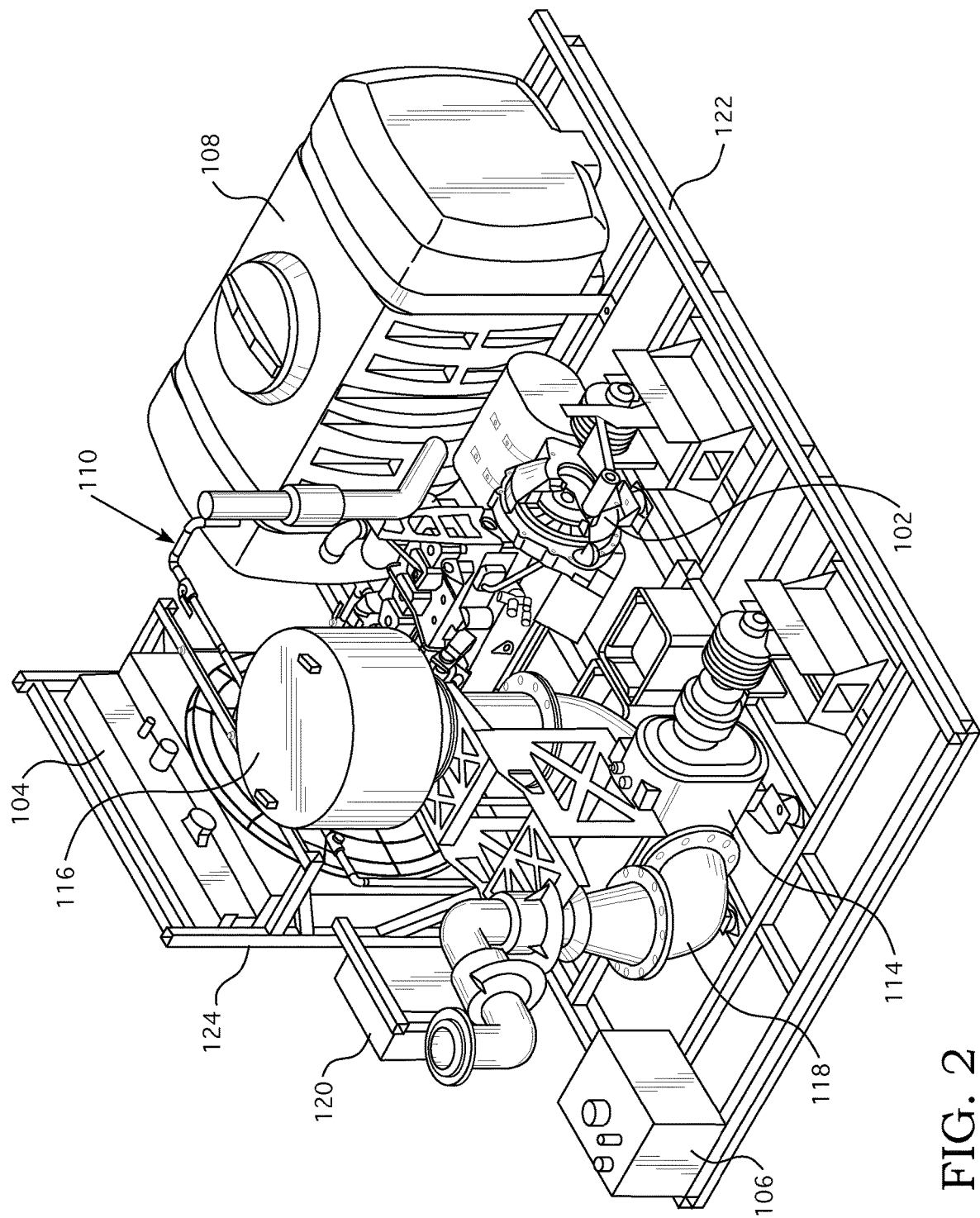
FIG. 2 is a perspective view of a fluid dispersion machinery according to one embodiment of the disclosed invention.
Figure 7:
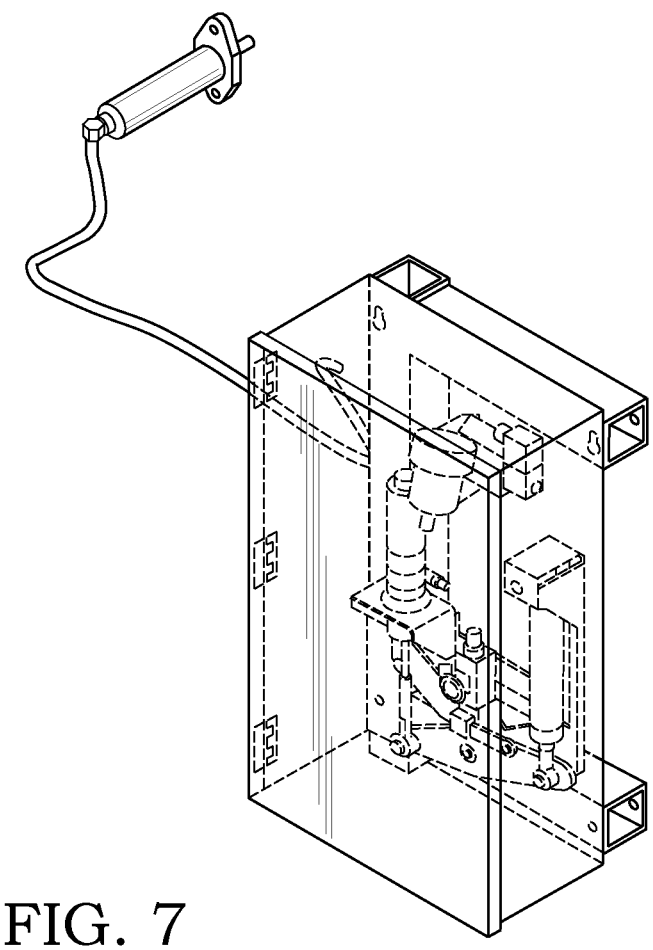
FIG. 7 illustrates a clutch actuator assembly of the fluid dispersion machinery according to one embodiment of the disclosed invention.

Generally, the fluid dispersion machinery is comprised of an engine assembly, a clutch actuator assembly, a fluid system assembly that attaches to the nozzle or multiple nozzles, an air compression assembly that attaches to the nozzle or multiple nozzles, and rigid framing that the assemblies can mount or attach to. More specifically, as illustrated in FIGS. 1 and 2, the fluid dispersion machinery can be controlled by an in-cab control system and can include, but is not limited to, an engine assembly comprised of an engine 102, a radiator 104, a fuel tank 106, and a fluid tank 108; a fluid system comprised of a fluid piping system 110 and a fluid pump 112; and air compression assembly comprised of an air compressor 114, an air compression intake and silencer 116, and air ducting 118; and a clutch assembly, illustrated in FIG. 7, comprised of a clutch 120. In some embodiments, the machinery, except for the in-cab control system, can be attached to a base frame 122 and the engine can be further (or alternatively) attached to a motor frame 124 that itself attaches to the base frame 122, thereby enabling easier movement of the fluid dispersion machinery on and off of the truck bed.

As mentioned above, specific parts of the fluid dispersion machinery, such as the fluid system assembly and the air compression assembly can attach to the nozzle and provide fluid and air directly to the nozzle. In some embodiments, this attachment point is flexible and enables a user to rotate the direction that the nozzle faces. More specifically, the nozzle itself may be the only part of the disclosed system that can rotate, and the fluid dispersion machinery may be fixed in place. In other embodiments, the nozzle and at least some of the fluid dispersion machinery, such as the air ducting 118, may be flexible and/or rotate.

A base frame 122 and motor frame 124 can provide attachment or mounting points for the rest of the machinery. Additionally, the base frame 122 can have fork lift access lifting points 126, which enable an individual to easily move the frames 122, 124 and the fluid dispersion machinery on and off of a truck bed or other elevated surface. The frames 122, 124 are rigid and can be made of metal such as, but not limited to, steel, stainless steel, aluminum, or any combination of these materials.

Figure 3:
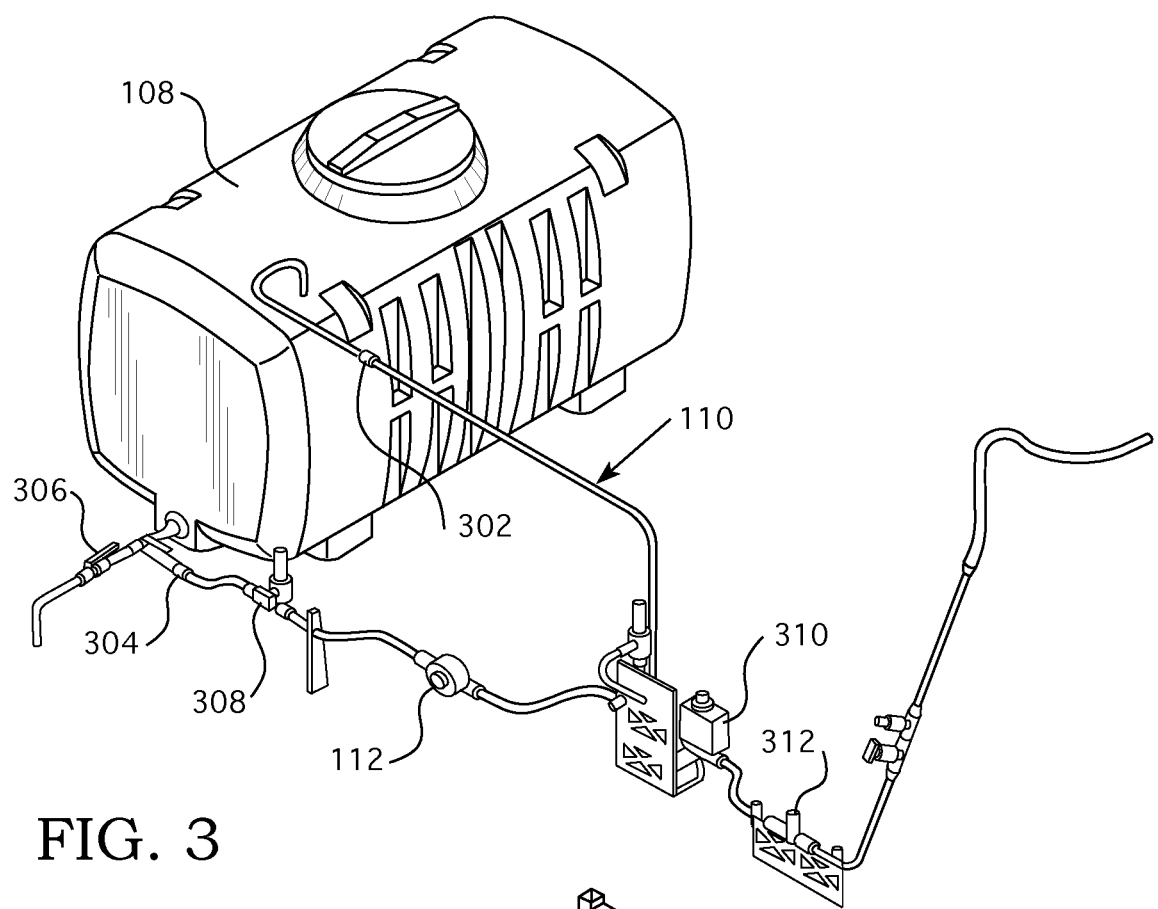
FIG. 3 illustrates a fluid system assembly of the fluid dispersion machinery according to one embodiment of the disclosed invention.
Figure 4:
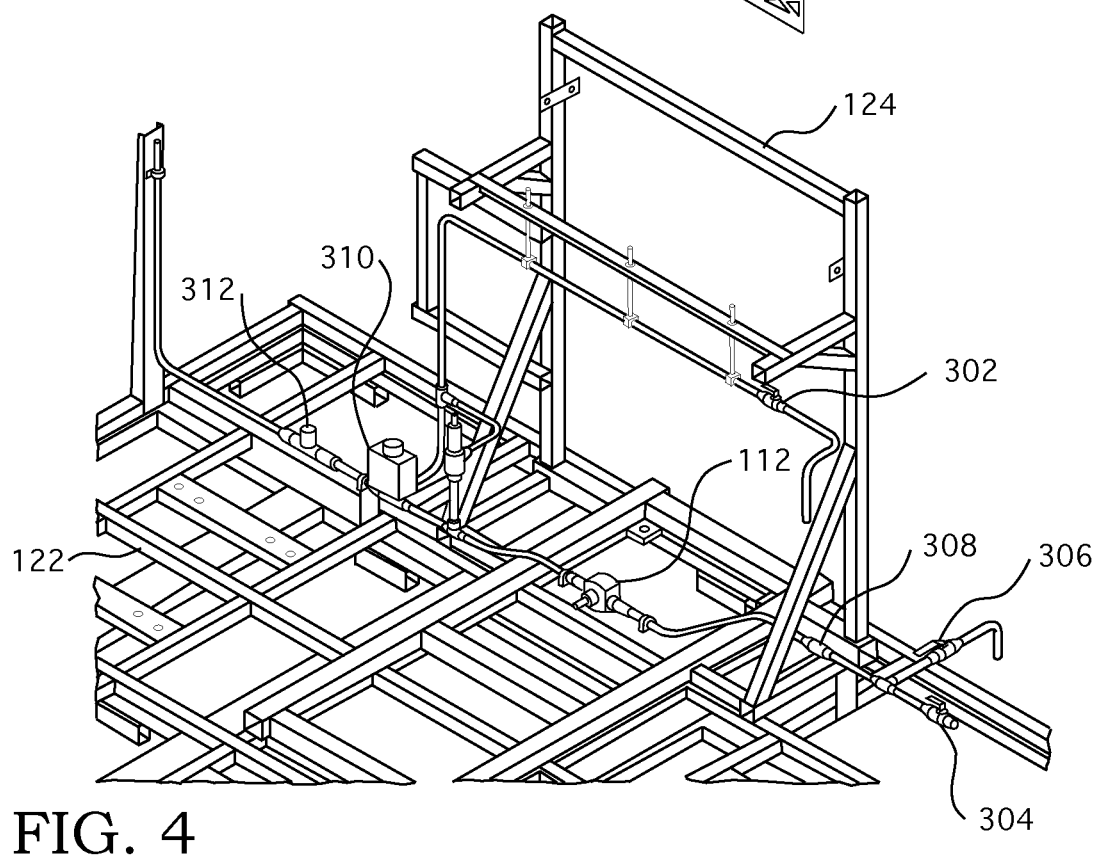
FIG. 4 illustrates a fluid piping system of the fluid system assembly of FIG. 3 mounted onto the base frame and motor frame of the fluid dispersion machinery according to one embodiment of the disclosed invention.

In some embodiments, a portion of the fluid dispersion machinery includes a fluid system assembly comprised of a fluid tank 108 for holding the fluid to be dispersed, a fluid piping system 110 for transporting fluid from the fluid tank 108 to the fluid dispersion nozzle, and a fluid pump 112 included in the fluid piping system 110 and run by the engine 102, as illustrated in FIGS. 3 and 4. The fluid piping system 110 can include, in addition to the fluid pump 112, an upper tank valve 302, a lower tank valve 304, a dump valve 306, a strainer 308, a bypass valve 310, and a flow meter 312. FIG. 3 illustrates the various fluid system assembly components. FIG. 4 illustrates one example of how the fluid tank 108, fluid piping system 110, and fluid pump 112 can mount onto the base frame 122 and motor frame 124.

Figure 5:
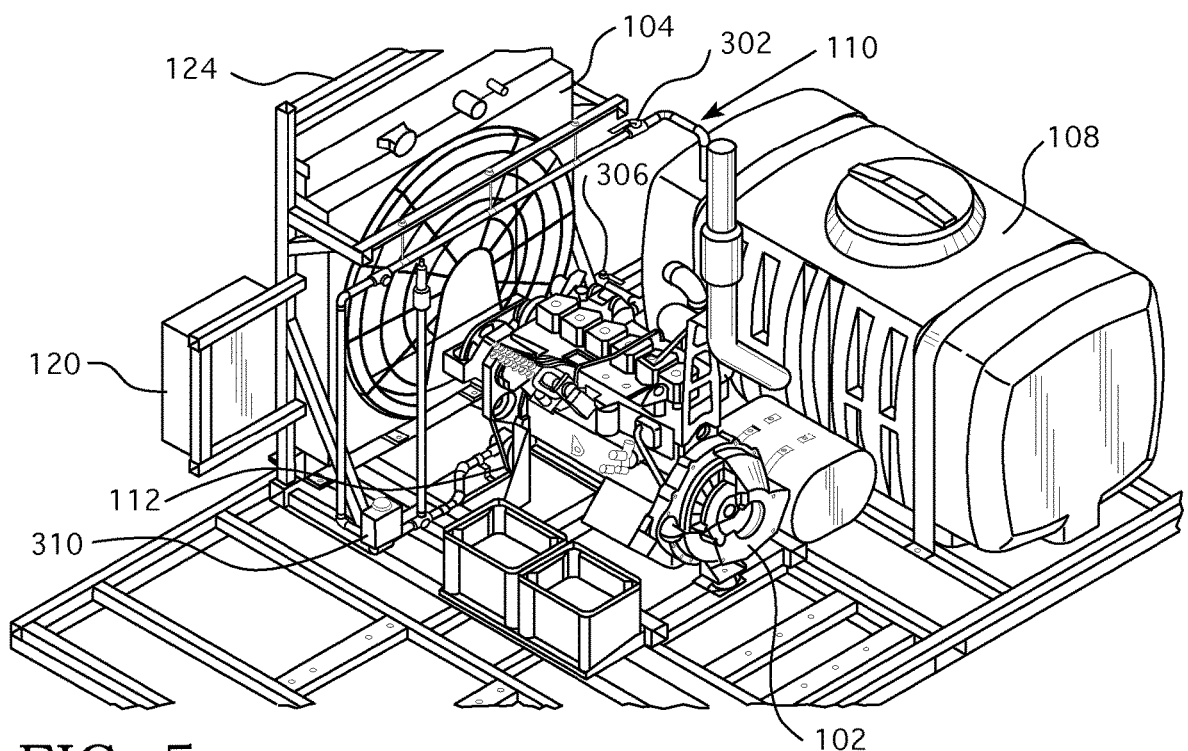
FIG. 5 illustrates a motor assembly and the fluid system assembly of FIG. 3 mounted onto the base frame and motor frame of the fluid dispersion machinery according to one embodiment of the disclosed invention.
Figure 6:
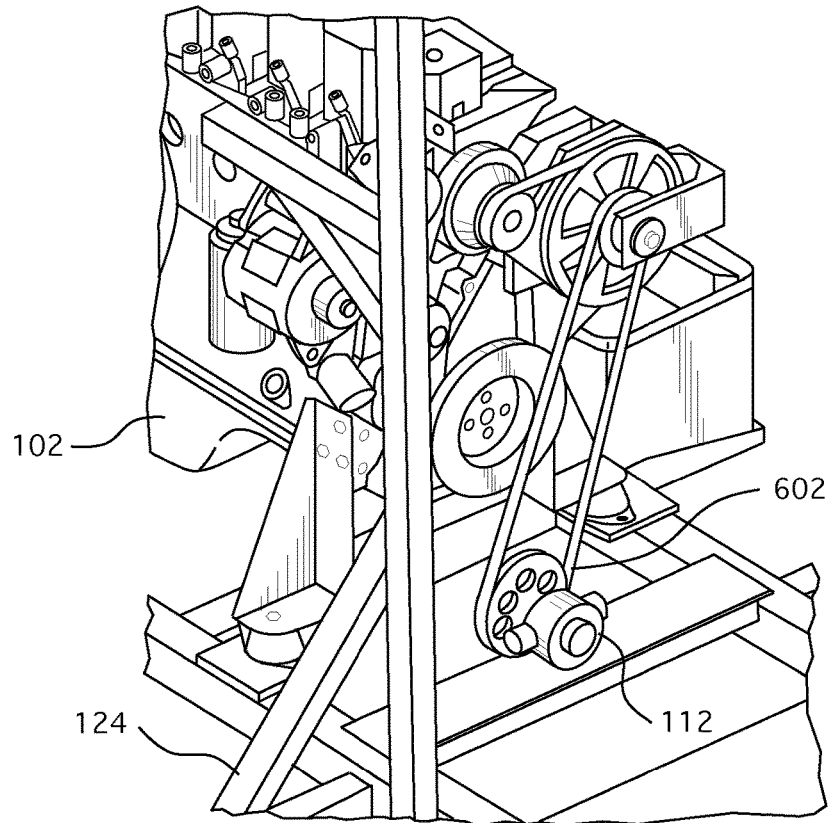
FIG. 6 illustrates a fluid pump attached to the motor of the fluid dispersion machinery according to one embodiment of the disclosed invention.

FIG. 5 illustrates how the engine 102 may be positioned relative to the fluid piping system 110. This positioning is important because the engine 102 powers the fluid pump 112. As illustrated in FIG. 6, a fluid pump belt 602 attaches to the engine 102 and the fluid pump 112. When the engine 102 is powered, it rotates the fluid pump belt 602, which then powers the fluid pump 112.

As described above, the vehicle-mounted fluid dispersion machinery can be controlled by an in-cab control system, illustrated in FIG. 8. In some embodiments, the in-cab control system can start the engine 102, the fluid pump 112, and the air compressor 114. Additionally, it can increase and decrease the engine RPMs, can track fuel levels, fluid levels, water temperature, and can turn work lights on and off, among other tasks.

What is claimed is:

1. A fluid dispersion nozzle comprising:
a nozzle body;
a hollow tip of the nozzle body centered within the nozzle body;
at least one contour enabled to adjust airflow;
an axial fluid injector including a fluid injector body having at least one flow entrance and at least one flow exit surrounded by the at least one contour and enabled to adjust fluid flow of a fluid in the fluid injector body; and
a resonator and a plunger positioned proximate the flow exit for aerosolizing the fluid;
wherein:
the hollow tip of the nozzle body is mechanically coupled to the fluid injector body and a nose cone;
the resonator is mechanically coupled to the fluid injector body via a first threaded connection; and
the plunger is mechanically coupled to the fluid injector body via a second threaded connection.

2. The fluid dispersion nozzle of claim 1, where the fluid dispersion nozzle is a supersonic, adjustable, dual-contour nozzle.

3. The fluid dispersion nozzle of claim 1, wherein the fluid dispersion nozzle is connected to fluid dispersion machinery.

4. The fluid dispersion nozzle of claim 3, wherein the fluid dispersion machinery is comprised of an air compressor and a fluid pump.

5. The fluid dispersion nozzle of claim 1, wherein the at least one contour is comprised of a main adjustable contour and an auxiliary adjustable contour.

6. The fluid dispersion nozzle of claim 5, wherein:
the main adjustable contour is positioned within the nozzle body and around the nose cone, and
the auxiliary adjustable contour is positioned within the nose cone and around at least a portion of the axial fluid injector and at least a portion of the fluid injector body.

7. The fluid dispersion nozzle of claim 6, wherein the main adjustable contour and the auxiliary adjustable contour have adjustable cross-sections.

8. The fluid dispersion nozzle of claim 1, wherein the hollow tip of the nozzle body contains the axial fluid injector.

9. The fluid dispersion nozzle of claim 8, wherein the hollow tip of the nozzle body is mechanically coupled to the nose cone via a spacer.

10. The fluid dispersion nozzle of claim 1, further comprising:
a fluid pump to transfer fluid from a fluid tank, through a pressure-regulating valve and hollow pylon and into the hollow tip of the nozzle body, wherein the pressure-regulating valve maintains the fluid pressure consistency of a predetermined rate;
a saddle that interfaces with the plunger;
a spring that pushes a steel ball toward an outer wall of the resonator, wherein the resonator has at least one axial slot and the steel ball engages with the at least one axial slot to lock the plunger in a specific position relative to the resonator;
a disperser body;
a nozzle head held in place by a clamping screw; and
wherein the disperser body and the nozzle head define at least a portion of an outer part of the fluid dispersion nozzle.

11. A method of fluid dispersion, the method comprising:
pumping pressurized air from an air compressor into a fluid dispersion nozzle;
pumping fluid through a fluid pump and into the fluid dispersion nozzle;
combining the air and the fluid in the nozzle to create a near-monodisperse cloud; and
distributing the near-monodisperse cloud into atmospheric air;
wherein:
the air flows from the air compressor, into the nozzle, and through an auxiliary contour and a main adjustable contour;
the fluid flows from the fluid pump through a pressure regulating valve, through a hollow pylon connected on a first end to the pressure regulating valve and on a second end to a hollow tip of a nozzle body of the fluid dispersion nozzle, and into the hollow tip of the nozzle body;
the fluid flows forward from the hollow tip of the nozzle body through an axial fluid injector having a fluid injector body until it hits a plunger;
the fluid reflects off the plunger and out through at least one flow exit of the fluid injector body proximate the plunger;
the air flowing through the auxiliary contour forces the plunger reflected fluid forward and into contact with a resonator;
the plunger reflected fluid reflects off the resonator and back toward the auxiliary contour and the main adjustable contour;
the air flowing through the main adjustable contour forces the resonator reflected fluid forward past an end of the nozzle and into the atmospheric air as the near-monodisperse cloud.

12. A disinfection method, the method comprising:
pumping pressurized air from an air compressor into a fluid dispersion nozzle;
pumping a disinfectant fluid through a fluid pump and into the fluid dispersion nozzle;
combining the air and the disinfectant fluid in the nozzle to create a near-monodisperse disinfectant cloud; and
distributing the near-monodisperse disinfectant cloud into atmospheric air;
wherein:
the air flows from the air compressor, into the nozzle, and through an auxiliary contour and a main adjustable contour;
the disinfectant fluid flows from the fluid pump through a pressure regulating valve, through a hollow pylon connected on a first end to the pressure regulating valve and on a second end to a hollow tip of a nozzle body of the fluid dispersion nozzle, and into the hollow tip of the nozzle body;
the disinfectant fluid flows forward from the hollow tip of the nozzle body through an axial fluid injector and a fluid injector body until it hits a plunger;
the disinfectant fluid reflects off the plunger and out through a flow exit in a side of the fluid injector body;
the air flowing through the auxiliary contour forces the plunger reflected disinfectant fluid forward and into contact with a resonator;

the plunger reflected disinfectant fluid reflects off the resonator and back toward the auxiliary contour and the main adjustable contour;

the air flowing through the main adjustable contour forces the resonator reflected disinfectant fluid forward past an end of the nozzle and into the atmospheric air as the near-monodisperse disinfectant cloud.

\* \* \* \* \*